(12) United States Patent
Barthe et al.

(10) Patent No.: US 8,166,332 B2
(45) Date of Patent: *Apr. 24, 2012

(54) TREATMENT SYSTEM FOR ENHANCING SAFETY OF COMPUTER PERIPHERAL FOR USE WITH MEDICAL DEVICES BY ISOLATING HOST AC POWER

(75) Inventors: Peter G. Barthe, Phoenix, AZ (US); Michael H. Slayton, Tempe, AZ (US); Vadim Kouklev, Tempe, AZ (US); Paul M. Jaeger, Mesa, AZ (US)

(73) Assignee: Ardent Sound, Inc., Mesa, AZ (US)

( * ) Notice: Subject to any disclaimer, the term of this patent is extended or adjusted under 35 U.S.C. 154(b) by 164 days.

This patent is subject to a terminal disclaimer.

(21) Appl. No.: 12/509,254

(22) Filed: Jul. 24, 2009

(65) Prior Publication Data

US 2010/0011236 A1 Jan. 14, 2010

Related U.S. Application Data

(63) Continuation of application No. 11/380,161, filed on Apr. 25, 2006, now Pat. No. 7,571,336.

(60) Provisional application No. 60/674,694, filed on Apr. 26, 2005.

(51) Int. Cl.
*G06F 1/26* (2006.01)
(52) U.S. Cl. .......................................... 713/340; 607/63
(58) Field of Classification Search .................... 607/63; 713/300, 340
See application file for complete search history.

(56) References Cited

U.S. PATENT DOCUMENTS 3,913,386 A 10/1975 Saglio
(Continued)

FOREIGN PATENT DOCUMENTS

DE 4029175 3/1992
(Continued)

OTHER PUBLICATIONS

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

(Continued)

*Primary Examiner* — Albert Wang
(74) *Attorney, Agent, or Firm* — Snell & Wilmer L.L.P.

(57) ABSTRACT

A method and system for enhancing computer peripheral safety is provided. In accordance with various aspects of the present invention, the exemplary method and system are configured to monitor and/or isolate alternating current (A.C.) supplies with and/or from any peripheral subsystems or devices. An exemplary method and system comprises an A.C. supply, a host computer system, and a peripheral subsystem or device connected to the host computer system, such as an ultrasound imaging and/or therapy peripheral, and an isolation subsystem configured for monitoring and/or isolating the A.C. supply from the peripheral subsystem or device. In accordance with an exemplary embodiment, an isolation subsystem comprises application software and associated modules and functions that when executed continuously monitors and/or polls the host computer's hardware and/or operating system for the presence of an isolated source, such as a battery, or an unisolated power source, such as through a battery charger and/or other connection path to the A.C. main supply. In accordance with other exemplary embodiments, an isolation subsystem can comprises a wireless or other safe/ isolated electrical link for connecting a patient contact device, and/or a verification link or other verification mechanisms configured between an isolation transformer and host computer to monitor or observe usage to power the host computer and peripheral subsystem.

3 Claims, 12 Drawing Sheets

U.S. PATENT DOCUMENTS

| | | |
|---|---|---|
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Tanezer |
| 4,441,486 A | 4/1984 | Pounds |
| 4,452,084 A | 6/1984 | Tanezer |
| 4,484,569 A | 11/1984 | Driller |
| 4,513,749 A | 4/1985 | Kino |
| 4,527,550 A | 7/1985 | Ruggera et al. |
| 4,528,979 A | 7/1985 | Marchenko |
| 4,567,895 A | 2/1986 | Putzke |
| 4,586,512 A | 5/1986 | Do-huu |
| 4,601,296 A | 7/1986 | Yerushalmi |
| 4,646,756 A | 3/1987 | Watmough |
| 4,663,358 A | 5/1987 | Hyon |
| 4,668,516 A | 5/1987 | Duraffourd et al. |
| 4,697,588 A | 10/1987 | Reichenberger |
| 4,757,820 A | 7/1988 | Itoh |
| 4,807,633 A | 2/1989 | Fry |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,893,624 A | 1/1990 | Lele |
| 4,896,673 A | 1/1990 | Rose et al. |
| 4,917,096 A | 4/1990 | Englehart |
| 4,973,096 A | 4/1990 | Jaworski |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,976,709 A | 12/1990 | Sand |
| 4,979,501 A | 12/1990 | Valchanov |
| 5,012,797 A | 5/1991 | Liang |
| 5,036,855 A | 8/1991 | Fry |
| 5,054,310 A | 10/1991 | Flynn |
| 5,054,470 A | 10/1991 | Fry |
| 5,115,814 A | 5/1992 | Griffith |
| 5,117,832 A | 6/1992 | Sanghvi |
| 5,123,418 A | 6/1992 | Saurel |
| 5,143,063 A | 9/1992 | Fellner |
| 5,143,074 A | 9/1992 | Dory |
| 5,150,711 A | 9/1992 | Dory |
| 5,150,714 A | 9/1992 | Green |
| 5,156,144 A | 10/1992 | Iwasaki |
| 5,158,536 A | 10/1992 | Sekins |
| 5,163,421 A | 11/1992 | Bernstein |
| 5,191,880 A | 3/1993 | McLeod |
| 5,209,720 A | 5/1993 | Unger |
| 5,224,467 A | 7/1993 | Oku |
| 5,230,334 A | 7/1993 | Klopotek |
| 5,230,338 A | 7/1993 | Allen et al. |
| 5,265,614 A | 11/1993 | Hayakawa et al. |
| 5,267,985 A | 12/1993 | Shimada et al. |
| 5,269,297 A | 12/1993 | Weng |
| 5,282,797 A | 2/1994 | Chess |
| 5,295,484 A | 3/1994 | Marcus |
| 5,304,169 A | 4/1994 | Sand |
| 5,321,520 A | 6/1994 | Inga et al. |
| 5,360,268 A | 11/1994 | Hayashi |
| 5,370,121 A | 12/1994 | Reichenberger |
| 5,371,483 A | 12/1994 | Bhardwaj |
| 5,380,280 A | 1/1995 | Peterson |
| 5,419,327 A | 5/1995 | Rohwedder |
| 5,435,311 A | 7/1995 | Umemura |
| 5,458,596 A | 10/1995 | Lax |
| 5,460,595 A | 10/1995 | Hall et al. |
| 5,471,988 A | 12/1995 | Fujio et al. |
| 5,492,126 A | 2/1996 | Hennige |
| 5,496,256 A | 3/1996 | Bock |
| 5,501,655 A | 3/1996 | Rolt |
| 5,503,320 A | 4/1996 | Webster et al. |
| 5,507,790 A | 4/1996 | Weiss |
| 5,520,188 A | 5/1996 | Hennige |
| 5,522,869 A | 6/1996 | Burdette |
| 5,524,620 A | 6/1996 | Rosenschein |
| 5,524,624 A | 6/1996 | Tepper |
| 5,526,812 A | 6/1996 | Dumoulin et al. |
| 5,526,814 A | 6/1996 | Cline et al. |
| 5,526,815 A | 6/1996 | Granz |
| 5,540,235 A | 7/1996 | Wilson |
| 5,558,092 A | 9/1996 | Unger |
| 5,560,362 A | 10/1996 | Sliwa et al. |
| 5,575,291 A | 11/1996 | Hayakawa |
| 5,575,807 A | 11/1996 | Faller |
| 5,577,502 A | 11/1996 | Darrow et al. |
| 5,577,991 A | 11/1996 | Akui et al. |
| 5,580,575 A | 12/1996 | Unger et al. |
| 5,601,526 A | 2/1997 | Chapelon |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,638,819 A | 6/1997 | Manwaring et al. |
| 5,647,373 A | 7/1997 | Paltieli |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,665,053 A | 9/1997 | Jacobs |
| 5,676,692 A | 10/1997 | Sanghvi |
| 5,685,820 A | 11/1997 | Riek et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,769,790 A | 6/1998 | Watkins |
| 5,795,297 A | 8/1998 | Daigle |
| 5,795,311 A | 8/1998 | Wess |
| 5,810,888 A | 9/1998 | Fenn |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,839,751 A | 11/1998 | Bonin |
| 5,840,032 A | 11/1998 | Hatfield et al. |
| 5,844,140 A | 12/1998 | Seale |
| 5,853,367 A | 12/1998 | Chalek et al. |
| 5,871,524 A | 2/1999 | Knowlton |
| 5,873,902 A | 2/1999 | Sanghvi |
| 5,879,303 A | 3/1999 | Averkiou et al. |
| 5,882,557 A | 3/1999 | Hayakawa |
| 5,891,034 A | 4/1999 | Bucholz |
| 5,904,659 A | 5/1999 | Duarte |
| 5,919,219 A | 7/1999 | Knowlton |
| 5,924,989 A | 7/1999 | Polz |

| | | | | | | |
|---|---|---|---|---|---|---|
| 5,928,169 | A | 7/1999 | Schatzle et al. | 6,428,477 B1 | 8/2002 | Mason |
| 5,931,805 | A | 8/1999 | Brisken | 6,428,532 B1 | 8/2002 | Doukas |
| 5,938,606 | A | 8/1999 | Bonnefous | 6,430,446 B1 | 8/2002 | Knowlton |
| 5,938,612 | A | 8/1999 | Kline-Schoder | 6,432,067 B1 | 8/2002 | Martin |
| 5,948,011 | A | 9/1999 | Knowlton | 6,432,101 B1 | 8/2002 | Weber |
| 5,957,844 | A | 9/1999 | Dekel | 6,436,061 B1 | 8/2002 | Costantino |
| 5,957,882 | A | 9/1999 | Nita et al. | 6,438,424 B1 | 8/2002 | Knowlton |
| 5,967,980 | A | 10/1999 | Ferre et al. | 6,440,071 B1 | 8/2002 | Slayton |
| 5,968,034 | A | 10/1999 | Fulmer | 6,440,121 B1 | 8/2002 | Weber |
| 5,971,949 | A | 10/1999 | Levin | 6,443,914 B1 | 9/2002 | Costantino |
| 5,984,882 | A | 11/1999 | Rosenschein | 6,453,202 B1 | 9/2002 | Knowlton |
| 5,997,471 | A | 12/1999 | Gumb et al. | 6,461,378 B1 | 10/2002 | Knowlton |
| 5,997,497 | A | 12/1999 | Nita et al. | 6,470,216 B1 | 10/2002 | Knowlton |
| 6,004,262 | A | 12/1999 | Putz et al. | 6,491,657 B2 | 12/2002 | Rowe |
| 6,007,499 | A | 12/1999 | Martin et al. | 6,500,121 B1 | 12/2002 | Slayton |
| 6,036,646 | A | 3/2000 | Barthe | 6,500,141 B1 | 12/2002 | Irion |
| 6,039,048 | A | 3/2000 | Silberg | 6,508,774 B1 | 1/2003 | Acker |
| 6,042,556 | A | 3/2000 | Beach et al. | 6,511,428 B1 | 1/2003 | Azuma |
| 6,049,159 | A | 4/2000 | Barthe | 6,514,244 B2 | 2/2003 | Pope |
| 6,050,943 | A | 4/2000 | Slayton | 6,524,250 B1 | 2/2003 | Weber |
| 6,059,727 | A | 5/2000 | Fowlkes | 6,540,679 B2 | 4/2003 | Slayton |
| 6,071,239 | A | 6/2000 | Cribbs | 6,554,771 B1 | 4/2003 | Buil et al. |
| 6,080,108 | A | 6/2000 | Dunham | 6,569,099 B1 | 5/2003 | Babaev |
| 6,086,535 | A | 7/2000 | Ishibashi | 6,595,934 B1 | 7/2003 | Hissong |
| 6,086,580 | A | 7/2000 | Mordon et al. | 6,599,256 B1 | 7/2003 | Acker |
| 6,090,054 | A | 7/2000 | Tagishi | 6,607,498 B2 | 8/2003 | Eshel |
| 6,093,883 | A | 7/2000 | Sanghvi | 6,623,430 B1 | 9/2003 | Slayton |
| 6,101,407 | A | 8/2000 | Groezinger | 6,626,854 B2 | 9/2003 | Friedman |
| 6,113,558 | A | 9/2000 | Rosenschein | 6,626,855 B1 | 9/2003 | Weng |
| 6,113,559 | A | 9/2000 | Klopotek | 6,638,226 B1 | 10/2003 | He et al. |
| 6,120,452 | A | 9/2000 | Barthe | 6,645,162 B2 | 11/2003 | Friedman |
| 6,135,971 | A | 10/2000 | Hutchinson et al. | 6,662,054 B2 | 12/2003 | Kreindel |
| 6,139,499 | A | 10/2000 | Wilk | 6,663,627 B2 | 12/2003 | Francischelli |
| 6,159,150 | A | 12/2000 | Yale et al. | 6,665,806 B2 | 12/2003 | Shimizu |
| 6,171,244 | B1 | 1/2001 | Finger et al. | 6,666,835 B2 | 12/2003 | Martin |
| 6,176,840 | B1 | 1/2001 | Nishimura | 6,685,640 B1 | 2/2004 | Fry |
| 6,183,426 | B1 | 2/2001 | Akisada | 6,692,450 B1 | 2/2004 | Coleman |
| 6,183,502 | B1 | 2/2001 | Takeuchi | 6,699,237 B2 | 3/2004 | Weber et al. |
| 6,183,773 | B1 | 2/2001 | Anderson | 6,719,449 B1 | 4/2004 | Laugharn |
| 6,190,323 | B1 | 2/2001 | Dias et al. | 6,719,694 B2 | 4/2004 | Weng |
| 6,190,336 | B1 | 2/2001 | Duarte | 6,825,176 B2 | 4/2004 | Mourad |
| 6,193,658 | B1 | 2/2001 | Wendelken et al. | 6,749,624 B2 | 6/2004 | Knowlton |
| 6,210,327 | B1 | 4/2001 | Brackett et al. | 6,775,404 B1 | 8/2004 | Pagoulatos et al. |
| 6,213,948 | B1 | 4/2001 | Barthe | 6,824,516 B2 | 11/2004 | Batten et al. |
| 6,216,029 | B1 | 4/2001 | Paltieli | 6,835,940 B2 | 12/2004 | Morikawa et al. |
| 6,233,476 | B1 | 5/2001 | Strommer et al. | 6,875,176 B2 | 4/2005 | Mourad et al. |
| 6,234,990 | B1 | 5/2001 | Rowe et al. | 6,887,239 B2 | 5/2005 | Elstrom |
| 6,241,753 | B1 | 6/2001 | Knowlton | 6,905,466 B2 | 6/2005 | Salgo |
| 6,246,898 | B1 | 6/2001 | Vesely et al. | 6,920,883 B2 | 7/2005 | Bessette |
| 6,268,405 | B1 | 7/2001 | Yao | 6,921,371 B2 | 7/2005 | Wilson |
| 6,273,864 | B1 | 8/2001 | Duarte | 6,932,771 B2 | 8/2005 | Whitmore |
| 6,287,257 | B1 | 9/2001 | Matichuk | 6,936,044 B2 | 8/2005 | McDaniel |
| 6,296,619 | B1 | 10/2001 | Brisken | 6,936,046 B2 | 8/2005 | Hissong |
| 6,301,989 | B1 | 10/2001 | Brown et al. | 6,953,941 B2 | 10/2005 | Nakano et al. |
| 6,311,090 | B1 | 10/2001 | Knowlton | 6,958,043 B2 | 10/2005 | Hissong |
| 6,315,741 | B1 | 11/2001 | Martin | 6,974,417 B2 | 12/2005 | Lockwood |
| 6,322,509 | B1 | 11/2001 | Pan et al. | 6,976,492 B2 | 12/2005 | Ingle |
| 6,322,532 | B1 | 11/2001 | D'Sa | 6,992,305 B2 | 1/2006 | Maezawa et al. |
| 6,325,540 | B1 | 12/2001 | Lounsberry et al. | 6,997,923 B2 | 2/2006 | Anderson |
| 6,325,769 | B1 | 12/2001 | Klopotek | 7,006,874 B2 | 2/2006 | Knowlton |
| 6,325,798 | B1 | 12/2001 | Edwards et al. | 7,020,528 B2 | 3/2006 | Neev |
| 6,350,276 | B1 | 2/2002 | Knowlton | 7,022,089 B2 | 4/2006 | Ooba |
| 6,356,780 | B1 | 3/2002 | Licato et al. | 7,058,440 B2 | 6/2006 | Heuscher et al. |
| 6,361,531 | B1 | 3/2002 | Hissong | 7,063,666 B2 | 6/2006 | Weng |
| 6,375,672 | B1 | 4/2002 | Aksan | 7,070,565 B2 | 7/2006 | Vaezy et al. |
| 6,377,854 | B1 | 4/2002 | Knowlton | 7,094,252 B2 | 8/2006 | Koop |
| 6,377,855 | B1 | 4/2002 | Knowlton | 7,115,123 B2 | 10/2006 | Knowlton |
| 6,381,497 | B1 | 4/2002 | Knowlton | 7,142,905 B2 | 11/2006 | Slayton |
| 6,381,498 | B1 | 4/2002 | Knowlton | 7,179,238 B2 | 2/2007 | Hissong |
| 6,387,380 | B1 | 5/2002 | Knowlton | 7,189,230 B2 | 3/2007 | Knowlton |
| 6,390,982 | B1 | 5/2002 | Bova et al. | 7,229,411 B2 | 6/2007 | Slayton |
| 6,405,090 | B1 | 6/2002 | Knowlton | 7,235,592 B2 | 6/2007 | Muratoglu |
| 6,409,720 | B1 | 6/2002 | Hissong | 7,258,674 B2 | 8/2007 | Cribbs |
| 6,413,253 | B1 | 7/2002 | Koop | 7,273,459 B2 | 9/2007 | Desilets |
| 6,413,254 | B1 | 7/2002 | Hissong | 7,297,117 B2 | 11/2007 | Trucco et al. |
| 6,419,648 | B1 | 7/2002 | Vitek | 7,347,855 B2 | 3/2008 | Eshel |
| 6,425,865 | B1 | 7/2002 | Salcudean | 7,393,325 B2 | 7/2008 | Barthe |
| 6,425,867 | B1 | 7/2002 | Vaezy | 7,491,171 B2 | 2/2009 | Barthe et al. |
| 6,425,912 | B1 | 7/2002 | Knowlton | 2001/0009997 A1 | 7/2001 | Pope |

| | | |
|---|---|---|
| 2001/0041880 A1 | 11/2001 | Brisken |
| 2002/0000763 A1 | 1/2002 | Jones |
| 2002/0040199 A1 | 4/2002 | Klopotek |
| 2002/0040442 A1 | 4/2002 | Ishidera |
| 2002/0055702 A1 | 5/2002 | Atala |
| 2002/0062077 A1 | 5/2002 | Emmenegger et al. |
| 2002/0062142 A1 | 5/2002 | Knowlton |
| 2002/0082528 A1 | 6/2002 | Friedman et al. |
| 2002/0082589 A1 | 6/2002 | Friedman et al. |
| 2002/0095143 A1 | 7/2002 | Key |
| 2002/0128648 A1 | 9/2002 | Weber |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169442 A1 | 11/2002 | Neev |
| 2002/0173721 A1 | 11/2002 | Grunwald et al. |
| 2002/0193831 A1 | 12/2002 | Smith |
| 2003/0018255 A1 | 1/2003 | Martin |
| 2003/0028113 A1 | 2/2003 | Gilbert et al. |
| 2003/0032900 A1 | 2/2003 | Ella |
| 2003/0036706 A1 | 2/2003 | Slayton |
| 2003/0040739 A1 | 2/2003 | Koop |
| 2003/0050678 A1 | 3/2003 | Sierra |
| 2003/0060736 A1 | 3/2003 | Martin et al. |
| 2003/0065313 A1 | 4/2003 | Koop |
| 2003/0074023 A1 | 4/2003 | Kaplan |
| 2003/0083536 A1 | 5/2003 | Eshel |
| 2003/0097071 A1 | 5/2003 | Halmann et al. |
| 2003/0125629 A1 | 7/2003 | Ustuner |
| 2003/0171678 A1 | 9/2003 | Batten et al. |
| 2003/0176790 A1 | 9/2003 | Slayton |
| 2003/0191396 A1 | 10/2003 | Sanghvi |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216795 A1 | 11/2003 | Harth |
| 2003/0220536 A1 | 11/2003 | Hissong |
| 2003/0220585 A1 | 11/2003 | Hissong |
| 2003/0236487 A1 | 12/2003 | Knowlton |
| 2004/0000316 A1 | 1/2004 | Knowlton |
| 2004/0001809 A1 | 1/2004 | Brisken |
| 2004/0002705 A1 | 1/2004 | Knowlton |
| 2004/0015106 A1 | 1/2004 | Coleman |
| 2004/0030227 A1 | 2/2004 | Littrup |
| 2004/0039312 A1 | 2/2004 | Hillstead |
| 2004/0039418 A1 | 2/2004 | Elstrom |
| 2004/0059266 A1 | 3/2004 | Fry |
| 2004/0073079 A1 | 4/2004 | Altshuler et al. |
| 2004/0073113 A1 | 4/2004 | Salgo |
| 2004/0073116 A1 | 4/2004 | Smith |
| 2004/0102697 A1 | 5/2004 | Evron |
| 2004/0143297 A1* | 7/2004 | Ramsey, III .................. 607/5 |
| 2004/0152982 A1 | 8/2004 | Hwang et al. |
| 2004/0186535 A1 | 9/2004 | Knowlton |
| 2004/0206365 A1 | 10/2004 | Knowlton |
| 2004/0210214 A1 | 10/2004 | Knowlton |
| 2004/0041880 A1 | 11/2004 | Brisken et al. |
| 2004/0217675 A1 | 11/2004 | Desilets |
| 2004/0249318 A1 | 12/2004 | Tanaka |
| 2004/0267252 A1 | 12/2004 | Washington |
| 2005/0033201 A1 | 2/2005 | Takahashi |
| 2005/0055073 A1 | 3/2005 | Weber |
| 2005/0070961 A1 | 3/2005 | Maki et al. |
| 2005/0074407 A1 | 4/2005 | Smith |
| 2005/0080469 A1 | 4/2005 | Larson |
| 2005/0113689 A1 | 5/2005 | Gritzky |
| 2005/0137656 A1 | 6/2005 | Malak |
| 2005/0154313 A1 | 7/2005 | Desilets |
| 2005/0154314 A1 | 7/2005 | Quistgaard |
| 2005/0154332 A1 | 7/2005 | Zanelli |
| 2005/0187495 A1 | 8/2005 | Quistgaard |
| 2005/0228281 A1 | 10/2005 | Nefos |
| 2005/0256406 A1 | 11/2005 | Barthe |
| 2005/0261584 A1 | 11/2005 | Eshel |
| 2005/0267454 A1 | 12/2005 | Hissong |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0111744 A1 | 5/2006 | Makin |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0206105 A1 | 9/2006 | Chopra |
| 2006/0241442 A1 | 10/2006 | Barthe |
| 2006/0261584 A1 | 11/2006 | Blackburn |
| 2006/0282691 A1 | 12/2006 | Barthe |
| 2006/0291710 A1 | 12/2006 | Wang et al. |
| 2007/0032784 A1 | 2/2007 | Gliklich |
| 2007/0035201 A1 | 2/2007 | Desilets |
| 2007/0055154 A1 | 3/2007 | Torbati |
| 2007/0055156 A1 | 3/2007 | Desilets |
| 2007/0087060 A1 | 4/2007 | Dietrich |
| 2007/0167709 A1 | 7/2007 | Slayton |
| 2007/0208253 A1 | 9/2007 | Slayton |
| 2008/0071255 A1 | 3/2008 | Barthe |
| 2008/0086054 A1 | 4/2008 | Slayton |
| 2008/0214966 A1 | 9/2008 | Slayton |
| 2008/0221491 A1 | 9/2008 | Slayton |
| 2008/0275342 A1 | 11/2008 | Barthe |
| 2008/0281237 A1 | 11/2008 | Slayton |
| 2008/0281255 A1 | 11/2008 | Slayton |
| 2008/0294073 A1 | 11/2008 | Barthe |

FOREIGN PATENT DOCUMENTS

| | | |
|---|---|---|
| DE | 10140064 | 3/2003 |
| DE | 10219217 | 11/2003 |
| DE | 20314479 | 3/2004 |
| EP | 0344773 | 12/1989 |
| EP | 1479412 | 11/1991 |
| EP | 0473553 | 4/1992 |
| EP | 0661029 | 7/1995 |
| EP | 1234566 | 8/2002 |
| EP | 1262160 | 12/2002 |
| GB | 2113099 | 8/1983 |
| JP | 3123559 | 5/1991 |
| JP | 03136642 | 6/1991 |
| JP | 4089058 | 3/1992 |
| JP | 7080087 | 3/1995 |
| JP | 7222782 | 8/1995 |
| JP | 2002078764 | 3/2002 |
| JP | 2003204982 | 7/2003 |
| JP | 2005323213 | 11/2005 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| WO | 9735518 | 10/1997 |
| WO | 9832379 | 7/1998 |
| WO | 9933520 | 7/1999 |
| WO | 9949788 | 10/1999 |
| WO | 0015300 | 3/2000 |
| WO | 0021612 | 4/2000 |
| WO | 0128623 | 4/2001 |
| WO | 0182777 | 11/2001 |
| WO | 0182778 | 11/2001 |
| WO | 0187161 | 11/2001 |
| WO | 0209813 | 2/2002 |
| WO | 0224050 | 3/2002 |

| | | |
|---|---|---|
| WO | 02292168 | 11/2002 |
| WO | 03070105 | 8/2003 |
| WO | 03077833 | 8/2003 |
| WO | 03086215 | 10/2003 |
| WO | 03099177 | 12/2003 |
| WO | 03101530 | 12/2003 |
| WO | 2005090978 | 9/2005 |
| WO | 2006036870 | 4/2006 |
| WO | 2006042168 | 4/2006 |
| WO | 2006042201 | 4/2006 |

OTHER PUBLICATIONS

Barthe et al., "Ultrasound therapy system and abiation results utilizing miniature imaging/therapy arrays," Ultrasonics Symposium, 2004 IEEE, Aug. 23, 2004, pp. 1792-1795, vol. 3.

Coon, Joshua et al., "Protein identification using sequential ion/ion reactions and tandem mass spectometry" Proceedings of the National Academy of Sciences of the USA, vol. 102, No. 27, Jul. 5, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444,456.

Daum et al., "Design and Evaluation of a Feedback Based Phased Array System for Ultrasound Surgery," IEEE Transactions on Ultrasonics, Feroelectronics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Gliklich et al., Clinical Pilot Study of Intense Ultrasound therapy to Deep Dermal Facial Skin and Subcutaneous Tissues, Arch Facial Plastic Surgery, Mar. 1, 2007, vol. 9.

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Husseini et al, "The Role of Cavitation in Acoustically Activated Drug Delivery," J. Control Release, Oct. 3, 2005, pp. 253-261, vol. 107(2).

Husseini et al. "Investigating the mechanism of accoustically activated uptake of drugs from Pluronic micelles," BMD Cancer 2002, 2:20k, Aug. 30, 2002, pp. 1-6.

Jenne, J., et al., "Temperature Mapping for High Energy US-Therapy", 1994 Ultrasonics Symposium, pp. 1879-1882.

Johnson, S.A., et al., "Non-Intrusive Measurement of Microwave and Ultrasound-Induced Hyperthermia by Acoustic temperature Tomography", Ultrasonics Symposium Proceedings, pp. 977-982 , 1977.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

Makin et al, "Miniaturized Ultrasound Arrays for Interstitial Ablation and Imaging," UltraSound Med. Biol. 2005, Nov. 1, 2005, pp. 1539-1550, vol. 31(11).

Makin et al., "Confirmal Bulk Ablation and Therapy Monitoring Using Intracorporeal Image-Treat Ultrasound Arrays", 4th International Symposium on Therapeutic Ultrasound, Sep. 19, 2004.

Manohar et al, "Photoaccoustic mammography laboratory prototype: imaging of breast tissue phantoms," Journal of Biomedical Optics, Nov./Dec. 2004, pp. 1172-1181, vol. 9, No. 6.

Mast et al, "Bulk Ablation of Soft Tissue with Intense Ultrasound; Modeling nad Experiments," J. Acoust. Soc. Am., Oct. 1, 2005, pp. 2715-2724, vol. 118(4).

Paradossi et al., "Poly(vinyl alcohol) as versatile biomaterial for potential biomedical applications," Journal of Materials Science: Materials in Medicine, 2003, pp. 687-691, vol. 14.

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Mitragotri, Samir; "Healing sound: the use of ultrasound in drug delivery and other therapeutic applications," Nature Reviews; Drug Delivery, pp. 255-260, vol. 4, Mar. 2005.

Sanghvi, N.T., et al., "Transrectal Ablation of Prostate Tissue Using Focused Ultrasound," 1993 Ultrasonics Symposium, IEEE, pp. 1207-1210.

Seip, Ralf, et al., "Noninvasive Detection of Thermal Effects Due to Highly Focused Ultrasonic Fiels," IEEE Symposium, pp. 1229-1232, vol. 2, Oct. 3-Nov. 1993.

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

Smith, Nadine Barrie, et al., "Non-Invasive In Vivo Temperature Mapping of Ultrasound Heating Using Magnetic Resonance Techniques", 1994 Ultrasonics Symposium, pp. 1829-1832, vol. 3.

Surry et al., "Poly(vinyl alcohol) cryogel phantoms for use in ultrasound and MR imaging," Phys. Med. Biol., Dec. 6, 2004, pp. 5529-5546, vol. 49.

Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.

Ueno, S., et al., "Ultrasound Thermometry in Hyperthermia", 1990 Ultrasonic Symposium, pp. 1645-1652.

Wang, H., et al., "Limits on Focused Ultrasound for Deep Hyperthermia", 1994 Ultrasonic Symposium, Nov. 1-4, 1994, pp. 1869-1872, vol. 3.

White et al "Selective Creation of Thermal Injury Zones in the Superficial Musculoaponeurotic System Using Intense Ultrasound Therapy," Arch Facial Plastic Surgery, Jan./Feb. 2007, vol. 9, No. 1.

Sassen, Sander, "ATI's R520 architecture, the new king of the hill?" http://www.hardwareanalysis.com/content/ article/1813, Sep. 16, 2005, 2 pages.

Wasson, Scott, "NVIDIA's GeFroce 7800 GTX graphics processor Power MADD," http://techreport.com/reviews/2005q2/geforce-7800gtx/index.x?pg=1, Jun. 22, 2005, 4 pages.

* cited by examiner

TREATMENT SYSTEM FOR ENHANCING SAFETY OF COMPUTER PERIPHERAL FOR USE WITH MEDICAL DEVICES BY ISOLATING HOST AC POWER

CROSS-REFERENCE TO RELATED APPLICATIONS

This application is a continuation of U.S. patent application Ser. No. 11/380,161, filed Apr. 25, 2006, entitled "Method and System for Enhancing Safety with Medical Peripheral Device by Monitoring if Host Computer is AC Powered," which claims priority to and the benefit of U.S. Provisional Application No. 60/674,964, filed on Apr. 25, 2005, entitled "Method and System for Enhancing Computer Peripheral Safety," both of which are incorporated by reference herein.

FIELD OF INVENTION

The present invention relates to computer peripherals and in particular to a method and system for enhancing electrical safety of peripheral systems and devices, such as those used for medical applications.

BACKGROUND OF THE INVENTION

Personal computers, or PCs, have become ubiquitous and exist in forms such as desktop, notebook (laptop), or several ultra-portable configurations among others. This pervasiveness has led to the development of a large assortment of increasingly sophisticated peripherals. In general, computer peripherals are devices that connect to a computing system to facilitate certain tasks and/or implement features not contained within the standard or base computer, including medical devices and other like equipment. However, the stringent electrical safety requirements and regulations which exist for medical equipment has circumscribed their use with PCs as peripherals. For example, electrical leakage currents must be severely limited to maintain patient isolation, yet computers and their peripherals are not commonly designed to accommodate such restrictions. One approach to alleviate these requirements is to employ an isolation transformer to power the computer and peripherals, but such a solution is expensive, bulky in size and weight, and relatively unsuited to portability. An alternative of custom-made power supplies is impractical, since a manufacturer of peripherals cannot design isolated power supplies for all conceivable PCs. What is needed is an effective means of providing computer peripheral safety.

SUMMARY OF THE INVENTION

A method and system for enhancing computer peripheral safety is provided. In accordance with various aspects of the present invention, the exemplary method and system are configured to monitor and/or isolate alternating current (A.C.) supplies with and/or from any peripheral subsystems or devices. An exemplary method and system comprises an A.C. supply, a host computer system, and a peripheral subsystem or device connected to the host computer system, such as an ultrasound imaging and/or therapy peripheral, and an isolation subsystem configured for monitoring and/or isolating the A.C. main supply from the peripheral subsystem or device.

In accordance with an exemplary embodiment, an isolation subsystem comprises application software and associated modules and functions that when executed continuously monitors and/or polls the host computer's hardware and/or operating system for the supply of power from an isolated power source, such as a battery supply, or from an unisolated power source, such as connection through a battery charger and/or other connection path to the A.C. main supply. If a connection to the A.C. main supply is detected, the application software shuts down or otherwise isolates the peripheral subsystem, thereby disallowing usage on a patient, and/or provides suitable warnings to a system user, such as requiring confirmation that an isolation subsystem/hardware is connected or operating. In accordance with an exemplary embodiment, the application software can also comprise A.C. detection modules configured to monitor the state of A.C. or battery power, to monitor the battery level, and give appropriate warnings and guidance to the user to facilitate control of any peripheral hardware or devices.

In accordance with another exemplary embodiment, an isolation subsystem comprises a wireless or other safe/isolated electrical link for connecting a patient contact device, such as a medical probe, to the peripheral subsystem to assure a high degree of isolation between the patient and electronics.

In accordance with another exemplary embodiment, an isolation subsystem comprises a verification link or other verification mechanisms configured between an isolation transformer and host computer to monitor or observe usage to power the host computer and peripheral subsystem.

BRIEF DESCRIPTION OF THE DRAWINGS

The subject matter of the invention is particularly pointed out in the concluding portion of the specification. The invention, however, both as to organization and method of operation, may best be understood by reference to the following description taken in conjunction with the accompanying drawing figures, in which like parts may be referred to by like numerals.

DETAILED DESCRIPTION

The present invention may be described herein in terms of various functional components and processing steps. It should be appreciated that such components and steps may be realized by any number of hardware components and software features configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of computer peripheral contexts and that the exemplary embodiments relating to a method for enhancing computer peripheral safety as described herein for medical probes and applications are merely indicative of exemplary applications for the invention. For example, the principles, features and methods discussed may be applied to any computer application and peripheral.

Figure 1:
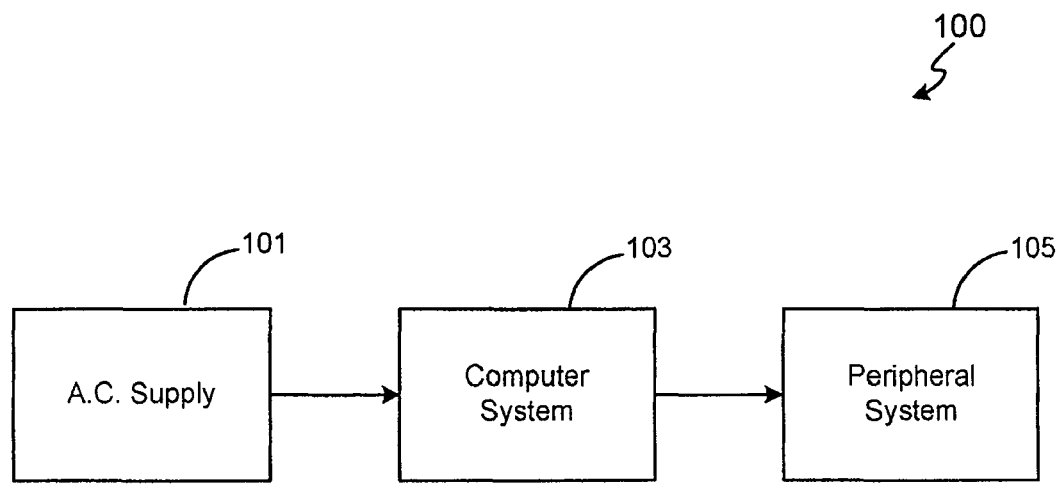
FIG. 1 is a block diagram of an exemplary system for enhancing electrical safety of peripheral systems in accordance with an exemplary embodiment of the present invention.

In accordance with various aspects of the present invention, a method and system for enhancing computer peripheral safety is provided. For example, in accordance with an exemplary embodiment, with reference to FIG. 1, an exemplary system 100 comprises an A.C. supply 101, a host computer system 103, and a peripheral subsystem or device 105 connected to host computer system 103. A.C. supply 101 suitably comprises an A.C. main supply or any other A.C. power source for supplying electrical power to equipment. Host computer system 103 is coupled to A.C. supply 101 and can comprise portable, laptop and/or notebook computers, desktop computers or any other host or operating computer configuration for operating peripheral subsystems and/or devices. Peripheral subsystem 105 can comprise any peripheral system or device, such as an ultrasound imaging and/or therapy peripheral system or device. For example, peripheral subsystem 105 can comprise systems and devices such as described in U.S. Pat. No. 6,440,071, entitled "Peripheral Ultrasound Imaging System", and hereby incorporated by reference. A host-peripheral communication link 106 can be operatively coupled between host computer 103 and peripheral subsystem 105 to facilitate control of peripheral subsystem 105, and can comprise any communication link or mechanism used between computers and peripheral devices for supplying power and/or communications. For example, communication link 106 can comprise a medical application link, such as for operatively coupling medical imaging and/or imaging/therapy systems to computer systems. To facilitate computer peripheral safety, system 100 further comprises an isolation subsystem configured for monitoring and/or isolating the A.C. supply 101 from peripheral subsystem 105.

Figure 2A:
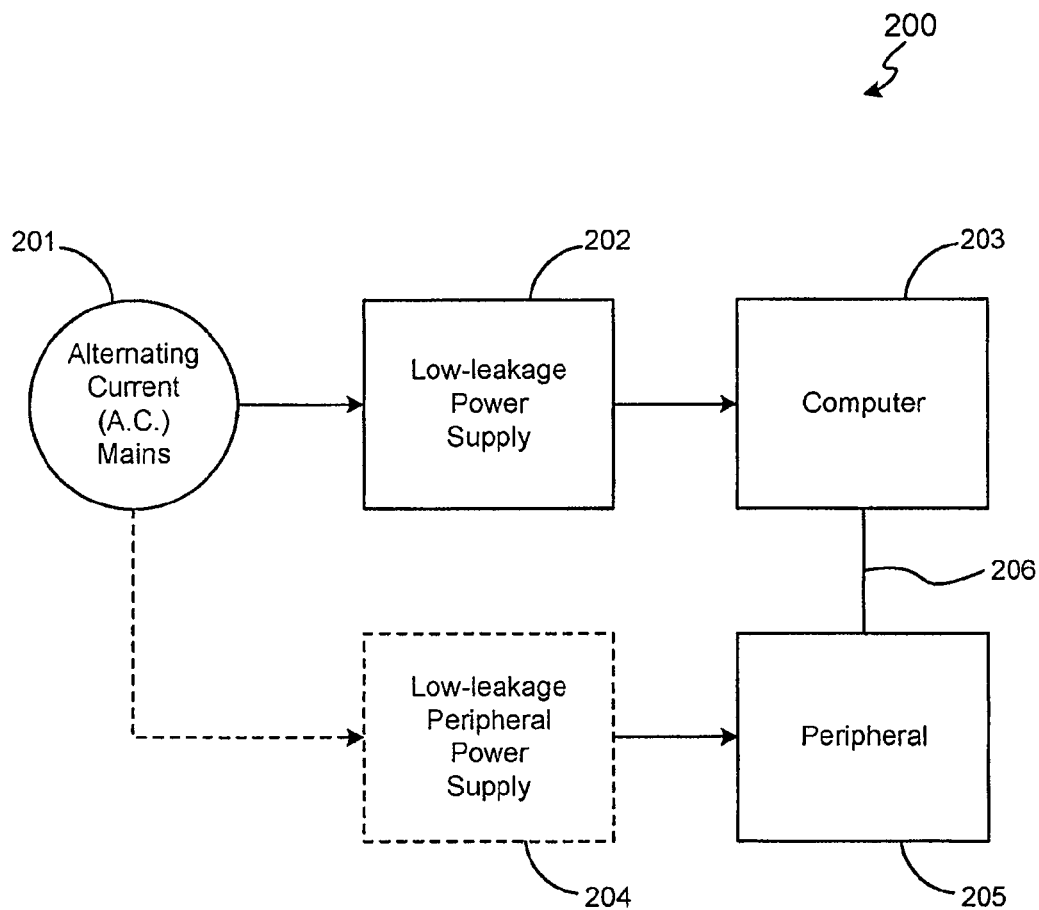
FIGS. 2A and 2B are block diagrams of a host computer, peripheral subsystem, power supplies and alternating current (A.C.) main supply for use with an isolation subsystem in accordance with an exemplary embodiment of the present invention.
Figure 2B:
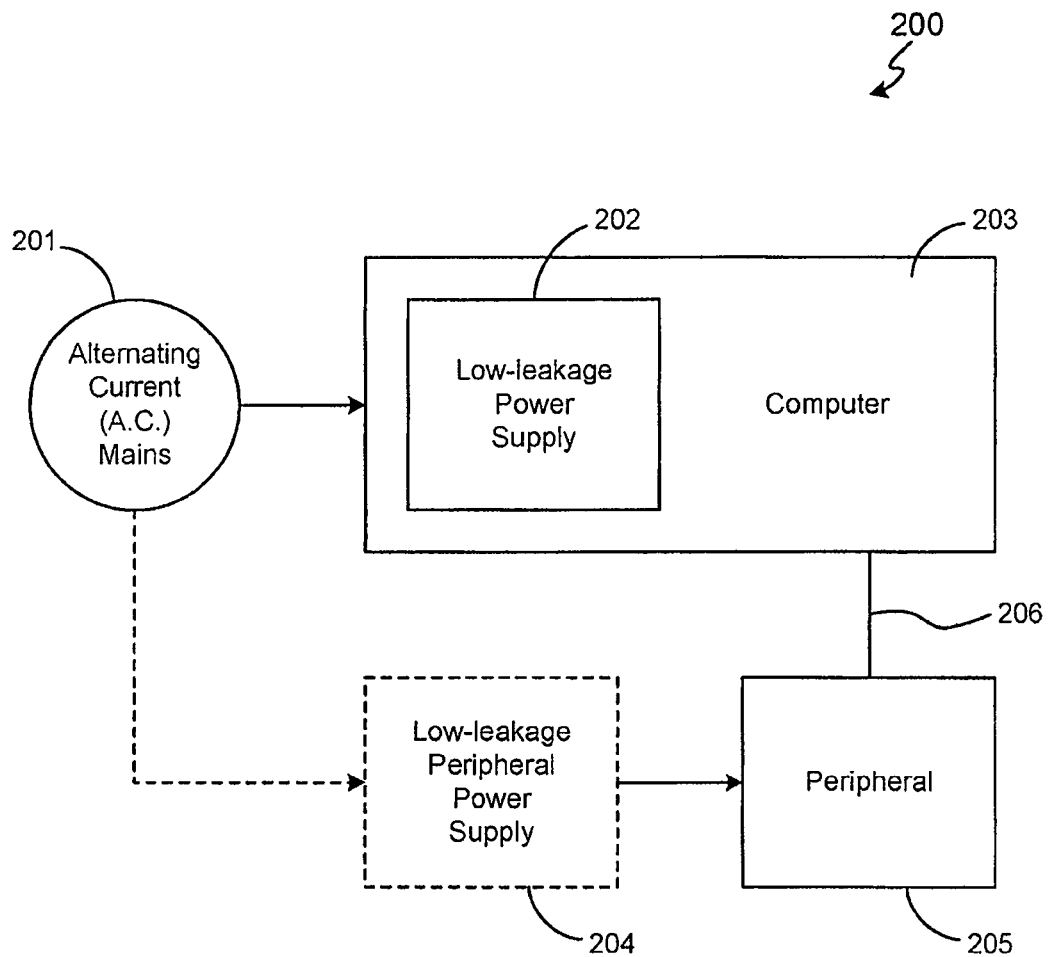

System 100 and components, A.C. supply 101, host computer 103 and peripheral 105, can be configured in various manners with an isolation subsystem for enhancing the safety of peripheral 105. For example, in accordance with an exemplary embodiment of the present invention, with reference to FIG. 2A, a peripheral safety system 200 can comprise a laptop or notebook computer 203 powered via a low-leakage/medical-grade power supply 202 that may also include a battery-backup system, including battery charger, or other uninterruptible power supply mechanism for host computer 203. Low-leakage/medical-grade power supply 202 can be suitably powered from A.C. main supply 201. In addition, an optional low-leakage/medical-grade peripheral power supply 204, powered from A.C. main supply 201, can also be coupled to peripheral 205 when additional power is needed for peripheral 205 and cannot be provided via communication link 206. Low leakage/medical-grade power supply 202 refers to a power supply or source of power which satisfies electric safety standards such as low-leakage, grounding, dielectric isolation, resistance to high potential voltages and transients. With reference to FIG. 2B, instead of laptop or notebook computers, host computer 203 can suitably comprise a desktop-style host computer and associated software 203. Typically desktop-style systems 203 differ from notebook-style systems in that power supply 202 is normally contained within the enclosure of computer 203.

An isolation subsystem can also be configured in various manners for monitoring and/or isolating A.C. supply 201 from peripheral subsystem or device 205. For example, to facilitate computer peripheral safety, a high degree of electrical isolation in one or both power supplies 202 and 204 can be provided, thus enhancing patient safety.

Figure 3:
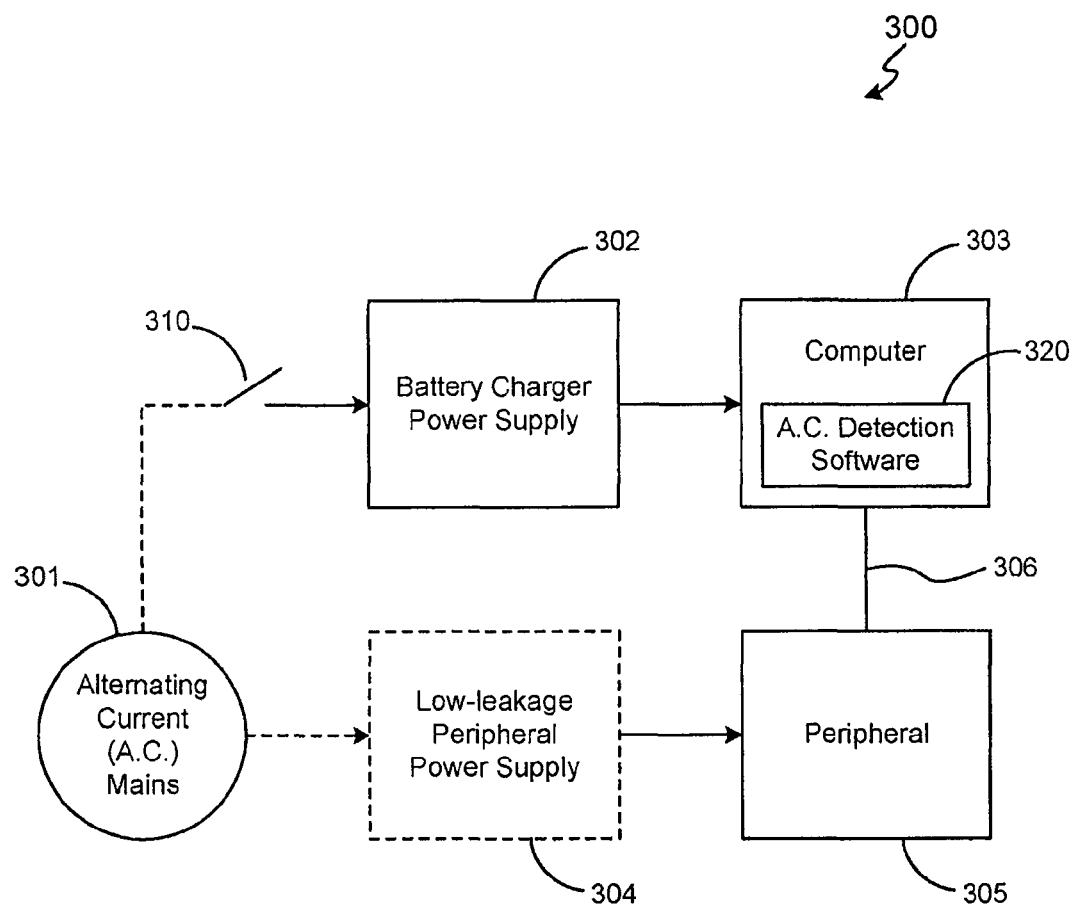
FIG. 3 is a block diagram of an exemplary system for enhancing electrical safety of peripheral systems with an isolation subsystem comprising A.C. detection software module in accordance with an exemplary embodiment of the present invention.

In accordance with another exemplary embodiment, with reference to FIG. 3, a peripheral safety system 300 can comprise a computer host and associated software 303 with an isolation subsystem comprising an A.C. detection software component 320. In this exemplary embodiment, host computer 303 is suitably powered via computer power supply/battery charger 302, powered from A.C. main 301. Power supply/battery charger 302 is configured to charge batteries for supplying an isolated power source to host computer 303. A.C. detection software component 320 is configured to detect through input devices 310 when PC battery charger 302 is connected to the A.C. main supply 301 (an unisolated power source) or disconnected (wherein an isolated power source comprising the charged battery supplies power) to the A.C. main supply 301 and disables (or re-enables) peripheral 305, e.g., disable or re-enable a medical application's functions. A.C. detection software component 320 can comprise any software and/or hardware configuration, including various input/output signals and components, for detecting when an A.C. supply is providing the source of power to host computer 303, e.g., detecting when a battery charger is connected and/or disconnected to A.C. main 301, and for suitably disabling one or more peripheral application functions, or otherwise for providing suitable warnings or other recommendations to the system user. By disabling at least some software/peripheral functionality, a high degree of electrical isolation is realized, and thus the patient safety is enhanced in medical applications.

Figure 4A:
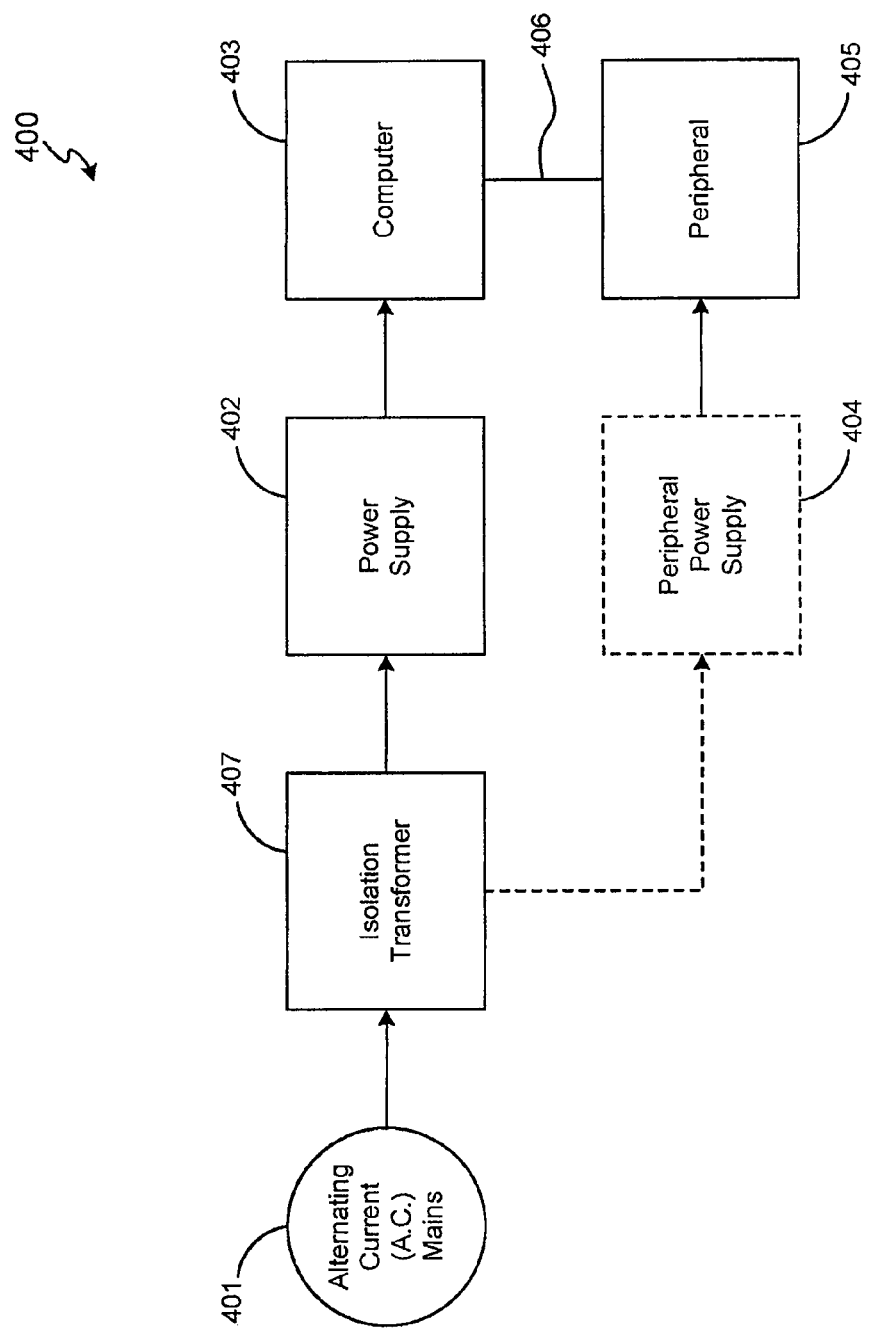
FIGS. 4A and 4B are block diagrams of exemplary systems for enhancing electrical safety of peripheral systems with an isolation subsystem and an isolation transformer in accordance with an exemplary embodiment of the present invention.
Figure 4B:
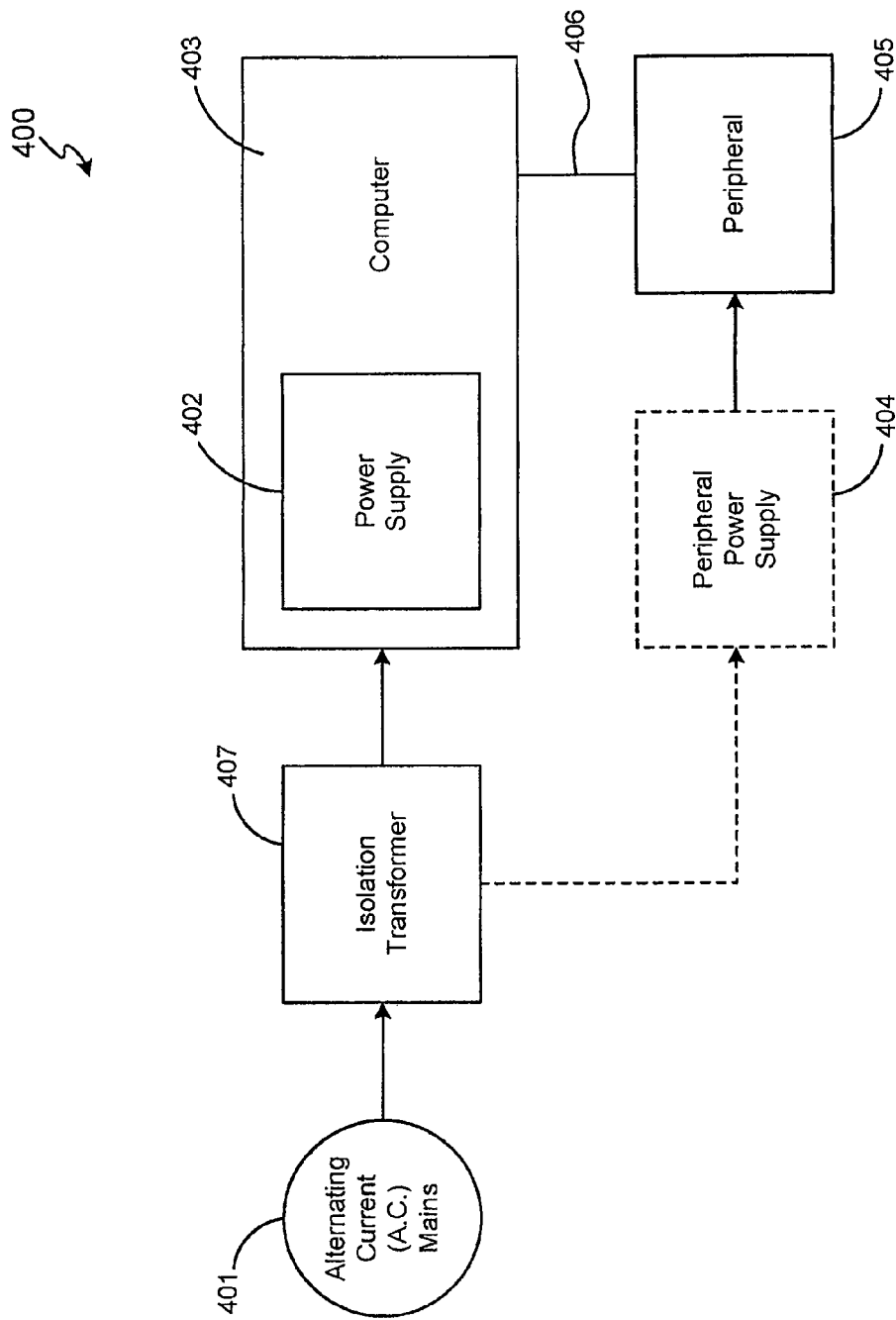

A.C. detection module 320 can be configured in addition to other isolation equipment and devices for facilitating safety. For example, with reference to FIGS. 4A and 4B, A.C. detection software can be resident within a laptop or notebook computer (FIG. 4A) or a desktop computer (FIG. 4B), with computer 403 further coupled to or including a power supply 402 coupled to an isolation transformer 407. Isolation transformer 407 can comprise any transformer configuration for isolating A.C. supplies from electrical equipment, such as computers and peripherals.

Figure 5A:
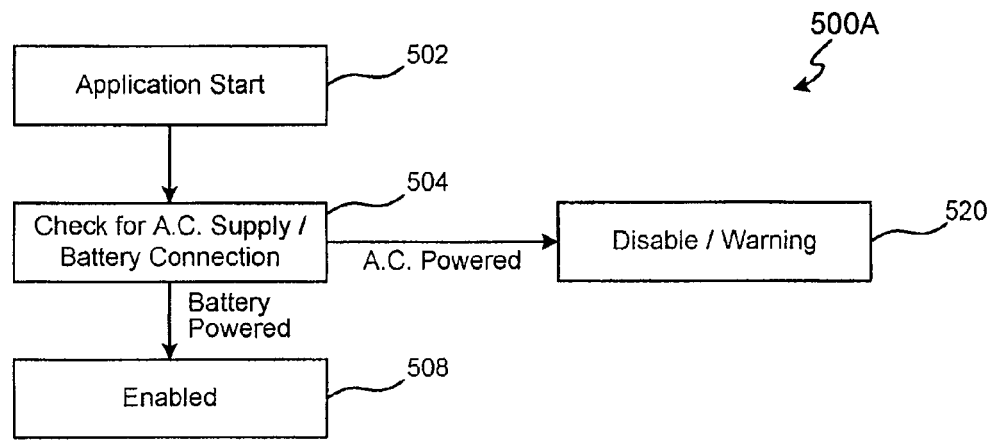
FIGS. 5A and 5B are flowcharts of operation for exemplary A.C. detection software modules in accordance with an exemplary embodiment of the present invention.

Detection module 320 can be provided in various operational steps through use of one or more algorithms and/or input/output devices for providing a method for enhancing computer peripheral safety. For example, with reference to FIG. 5A, in accordance with an exemplary embodiment, an exemplary method 500A may comprise A.C. detection module configured into application software and associated modules. As soon as the application software initiates or starts

502, the detection module checks for operative connection to an unisolated power source, e.g., an A.C. supply, or to an isolated power source, e.g., battery power 504. If not battery powered (i.e., if powered by or otherwise operatively connected to the A.C. supply, such as through the battery charger) the detection module moves to disabling functions and/or displaying a warning 520. However, if detection module determines the host computer is powered directly by battery power (e.g., the batter charger is not plugged in to the A.C. supply) 506, all normal hardware and software functionality is enabled 508, and the system continues operating.

Figure 5B:
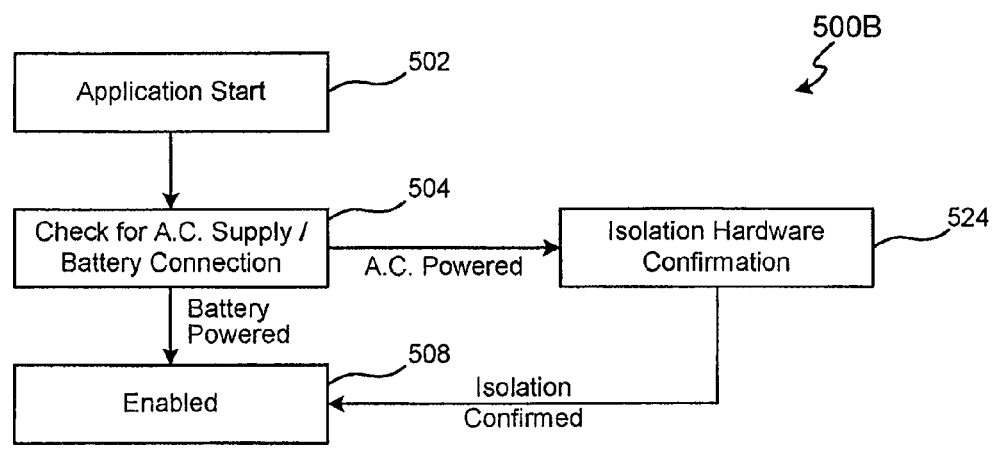

In accordance with another exemplary embodiment, with reference to FIG. 5B, instead of disabling functions or warning the system user to terminate use of any peripheral devices if a connection to the A.C. main supply is detected 520, the application software and associated modules request confirmation from the system user that isolation hardware is being used 524. If the system user confirms that appropriate isolation hardware is installed and operating, any normal hardware and software functionality is enabled 508, and usage of the peripheral device is allowed; if isolation hardware is not in place or operating, then peripheral device usage is disallowed. Such a confirmation 524 can be manually confirmed by the system user, and/or through input/output devices configured to determine the presence of isolation hardware, such as isolation transformers and devices.

Figure 6:
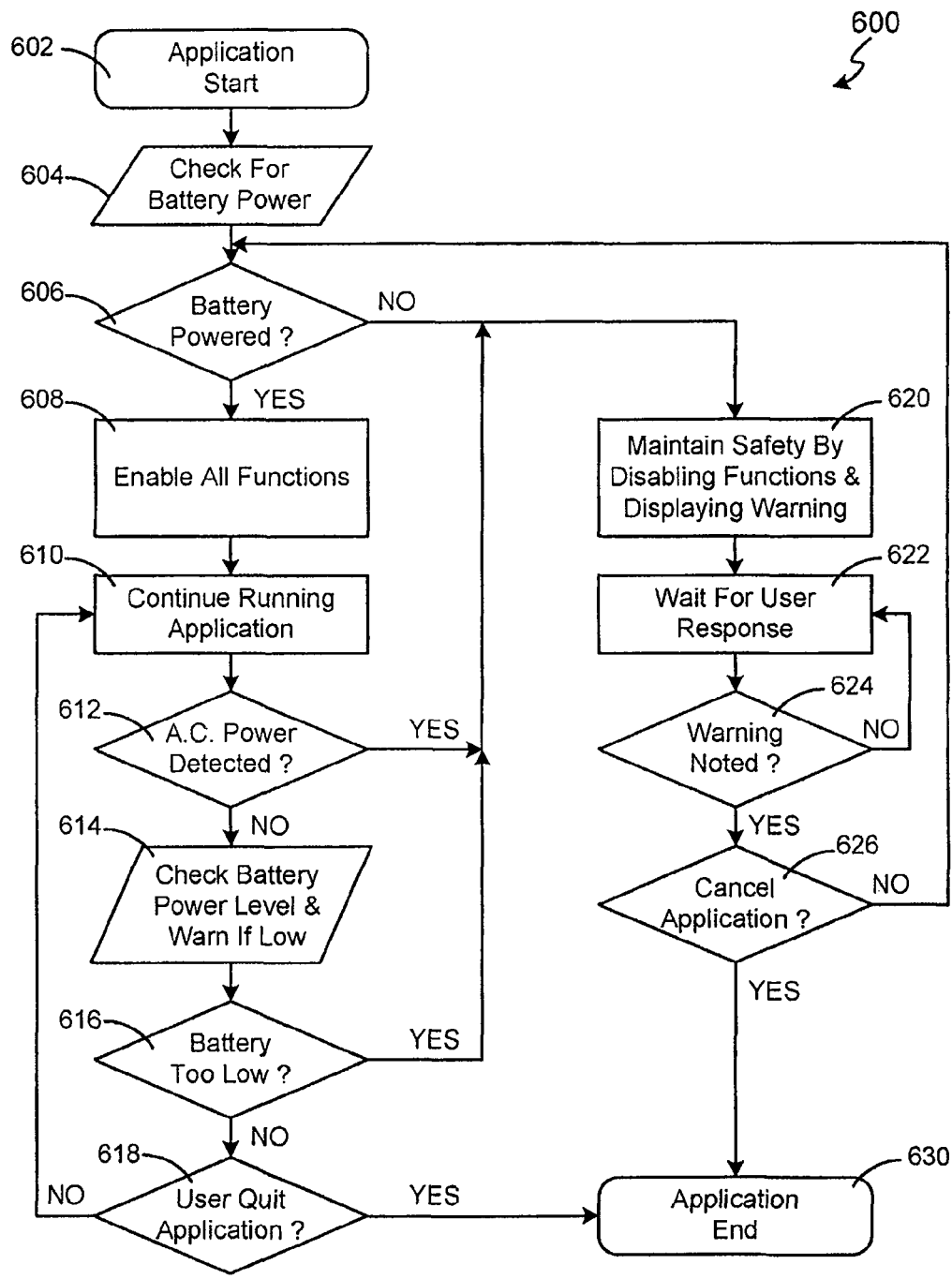
FIG. 6 is a flowchart of a A.C. detection software module in accordance with another exemplary embodiment of the present invention.

With reference to FIG. 6, another exemplary method may comprise additional monitoring and/or isolation functions. For example, as soon as the application software initiates or starts 602, the detection module checks for operative connection to an unisolated power supply, e.g., the A.C. supply, or to an isolated power supply, e.g., to battery power 604. If not battery powered (e.g., if powered by A.C. supply) the detection module moves to disabling functions and/or displaying a warning 620. However, if the detection module determines the host computer is powered directly by battery supply (e.g., the batter charger is not plugged in to the A.C. supply) 606, all normal hardware and software functionality is enabled 608, and the system continues operating or running 610 while the presence of A.C. charging is constantly scanned for by the detection module 612, e.g., the presence of A.C. charging is constantly scanned in the detection software and/or detected instantly via operating system interrupts, such as power change broadcast messages. Thereafter, if the connection to A.C. power is detected, the detection module moves to disabling functions and/or displaying a warning 620. However, if no such detection occurs, the detection module also checks whether the battery level has gone low. If the battery supply level is low, a warning can be issued to the user 614. If the battery level goes too low, e.g. almost empty, the detection module can also resort to disabling functions 620 to maintaining safety, and/or the user can request to quit the application 618 and end operation 630, or to continue the application running 610.

The process of disabling/warning 620 maintains safety by disabling functions (hardware and/or software), displaying a warning, and/or waiting for a user acknowledgement 622 if a connection to A.C. power is detected or the battery is very low or nearly empty. For example, as a warning is acknowledged 624, the user can be given the option to cancel the application 626 and thereby ending 630; if the user decides not to cancel operation, the detection module can continue with monitoring/re-checking for battery power 606. Thus, the system functionality in which safety and patient isolation is essential can be controlled such that the functionality is not re-enabled until the system is confirmed to be supplied on battery power. Such a configuration can allow the user to perform some functions, such as saving images or other processes, while safety-critical features and patient isolation can be preserved.

Figure 7A:
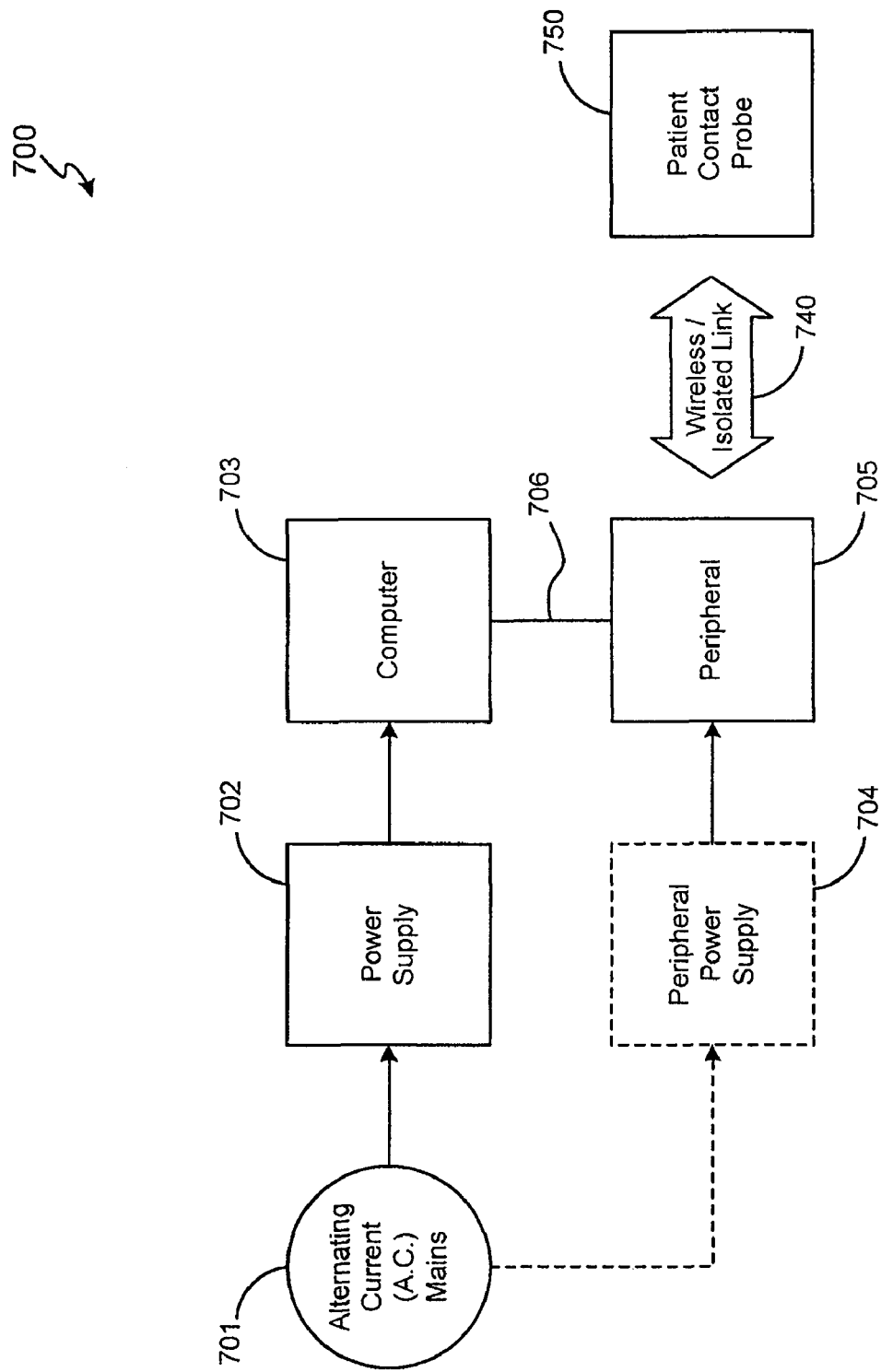
FIGS. 7A and 7B are block diagrams of exemplary systems for enhancing electrical safety of peripheral systems with an isolation subsystem comprising a wireless or other isolated link to a patient contact probe in accordance with an exemplary embodiment of the present invention.
Figure 7B:
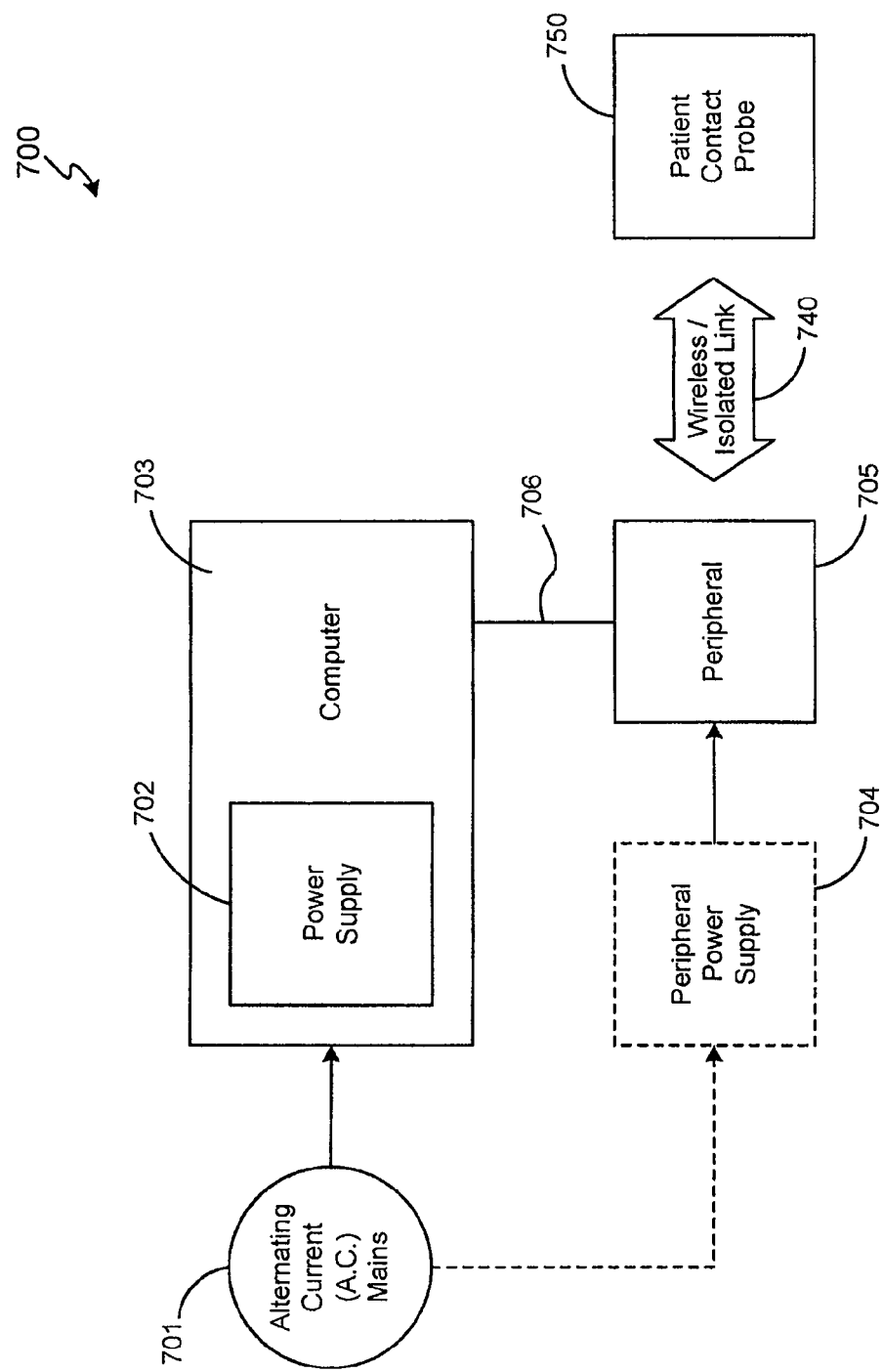

In accordance with another exemplary embodiment, with reference to FIGS. 7A (laptop or portable PC) and 7B (desktop PC), peripheral safety system 700 can include an isolation subsystem comprising a wireless and/or other isolated electrical link 740 coupled between a peripheral system 705 and a peripheral device 750, such as a patient contact probe. Some examples of wireless and/or other isolated electrical links include wireless USB (wireless Universal Serial Bus), certified wireless USB, wireless Ethernet or IEEE 802.11 based technology, Wi-Fi, WiMedia, Bluetooth, proprietary radio transceivers and associated technology, cellular or other radio network based wireless, and optical wireless such as IrDA. By providing a wireless and/or electrically safe or low-leakage isolated link 740 between the peripheral/computer and patient contact probe 750, patient safety is enhanced. Isolated link 740 may be provided at any suitable point within system 700. For example, components, part or whole, of computer 703 and/or peripheral 705 may be disposed on either side of isolated link 740, so long as a high degree of isolation between A.C. main supply 701 and patient are maintained.

Figure 8A:
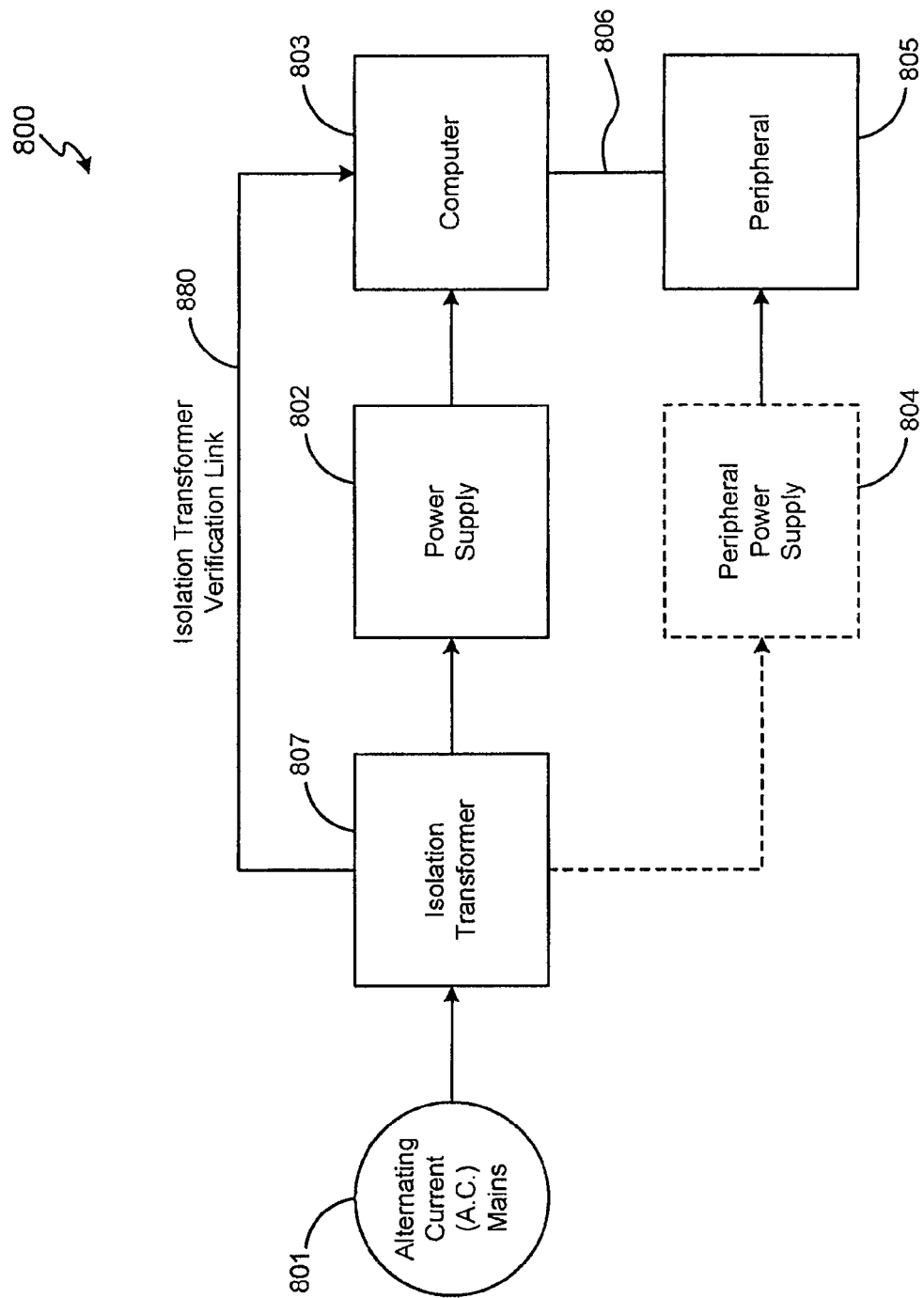
FIGS. 8A and 8B are block diagrams of exemplary systems for enhancing electrical safety of peripheral systems with an isolation subsystem comprising an isolation transformer verification link in accordance with an exemplary embodiment of the present invention.
Figure 8B:
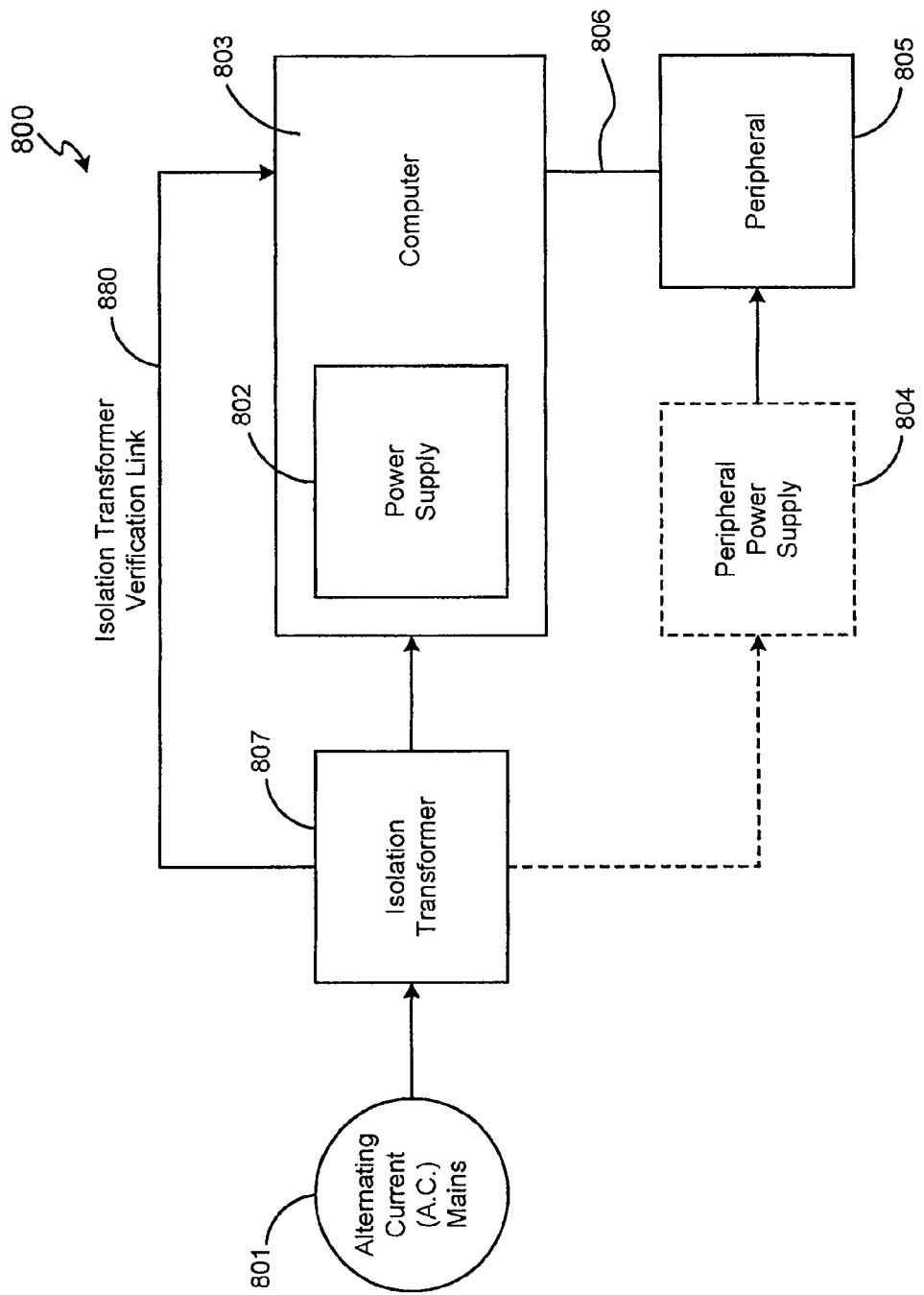

In accordance with another exemplary embodiment of the present invention, with reference to FIGS. 8A (laptop or portable PC) and 8B (desktop PC), a peripheral safety system 800 can include an isolation subsystem comprising an isolation transformer 807 configured with an isolation transformer verification link 880 configured in between isolation transformer 807 and computer 803. Isolation transformer 807 can comprise a low-leakage medical-grade isolation transformer or other like systems. As such, isolation transformer 807 provides a high degree of electrical isolation only when it is used as intended, thus isolation transformer verification link 880 is configured to confirm with computer 803 and/or peripheral 805 that isolation transformer 807 is present and in proper use. Isolation transformer verification link 980 suitably comprises a feedback mechanism that can contain software and/or hardware functionality and protection keys to assure that isolation transformer 807 and/or other components in system 800 are being used in the appropriate configuration to maintain safety. Isolation transformer verification link 880 can comprise any feedback configuration configured to monitor an isolation transformer and/or other electrical or control components and/or any of the appropriate operations of peripheral device 805. For example, in accordance with an exemplary embodiment, isolation transformer verification link 880 can comprise a wire or other coupling device connected into a USB port of computer 803 from isolation transformer 807 to allow monitoring of transformer operation. However, isolation transformer verification link 880 can comprise any other communication link, e.g., cable and/or wireless.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. For example, although the exemplary embodiments illustrate one configuration for an isolation subsystem, it should be noted that various exemplary embodiments for an isolation subsystem can also comprise a combination of detection module and isolation transformer and/or wireless/isolated links. These and other changes or modifications are intended to be included within the scope of the present invention, as set forth in the following claims.

The invention claimed is:

1. A treatment system configured for enhanced computer peripheral safety for use with medical devices, said treatment system comprising:
   an A.C. main power supply;
   a host computer system configured with a power supply, said host computer system further coupled to said A.C. main power supply;
   a peripheral system coupled to said host computer system and configured for control of medical devices; and
   an isolation subsystem configured for isolating said A.C. power supply from said peripheral system during operation of said peripheral system;
   wherein said isolation subsystem comprises a detection module configured within said host computer system for monitoring supply of power from said A.C. power supply to said host computer system; wherein said detection module is configured to disable at least one function of said peripheral system when said A.C. power supply is supplying power to said host computer system; and wherein said power supply of said host computer further comprises an A.C. powered battery charger and an isolated battery, and wherein said detection module is configured to determine whether said A.C. power supply is supplying power through said battery charger or whether said isolated battery is supplying power to said host computer system.

2. The system according to claim 1, wherein said detection module is further configured to monitor power levels of said isolated battery and provide at least one of a disabling function and a warning function to a user if said power levels are below acceptable levels.

3. A treatment system configured for enhanced computer peripheral safety for use with medical devices, said treatment system comprising:
   an A.C. main power supply;
   a host computer system configured with a power supply, said host computer system further coupled to said A.C. main power supply;
   a peripheral system coupled to said host computer system and configured for control of medical devices; and
   an isolation subsystem configured for isolating said A.C. power supply from said peripheral system during operation of said peripheral system; wherein said isolation subsystem comprises an isolation transformer and a verification link, each configured between said A.C. power supply and said host computer; wherein said verification link comprises a feedback mechanism configured to monitor operations of at least one of isolation transformer and said peripheral system; wherein said verification link comprises a wired connection from said isolation transformer to a USB port of said host computer.

* * * * *